(12) United States Patent
Allee et al.

(10) Patent No.: US 6,304,784 B1
(45) Date of Patent: Oct. 16, 2001

(54) FLEXIBLE PROBING DEVICE AND METHODS FOR MANUFACTURING THE SAME

(75) Inventors: David R. Allee, Phoenix; Link C. Jaw, Scottsdale, both of AZ (US)

(73) Assignee: Arizona Board of Regents, acting for and on behalf of Arizona State University, Tempe, AZ (US)

( * ) Notice: Subject to any disclaimer, the term of this patent is extended or adjusted under 35 U.S.C. 154(b) by 0 days.

(21) Appl. No.: 09/333,353

(22) Filed: Jun. 15, 1999

(51) Int. Cl.[7] ...................................................... A61N 1/00
(52) U.S. Cl. ........................... 607/116; 600/372; 600/378
(58) Field of Search ...................... 604/21; 600/373–374, 600/377–378, 381, 341, 339; 607/122

(56) References Cited

U.S. PATENT DOCUMENTS 5,824,026 * 10/1998 Diaz .

OTHER PUBLICATIONS

"High–Frequency Unilateral Thalamic Stimulation in the Treatment of Essential and Parkinsonian Tremor", W. Koller et al., Annals of Neurology, vol. 42, No. 3, pp. 292–299 (Sep. 1997).
"A High–Yield IC–Compatible Multichannel Recording Array", K. Najafi, K.D. Wise and T. Mochizuki, vol. ED–32, No. 7, pp. 1206–1211 (Jul. 1985).
"An Implantable Multielectrode Array with On–Chip Signal Processing", K. Najafi and K.D. Wise, IEEE Journal of Solid State Circuits, vol. 21, No. 6, pp. 1035–1044 (Dec. 1986).
"An Implantable CMOS Circuit Interface for Multiplexed Microelectrode Recording Arrays", Jin Ji and K.D. Wise, IEEE Journal of Solid State Circuits, vol. 27, No. 3, pp. 433–443 (Mar. 1992).
"A Three Dimensional Microelectrode Array For Chronic Neural Recording", A.C. Hoogerwerf and K.D. Wise, IEEE Transactions of Biomedical Engineering, vol. 41, No. 12, pp. 1136–1146 (Dec. 1994).
"A Multichannel Neural Probe for Selective Chemical Delivery at the Cellular Level", J. Chen, K.D. Wise, J.F. Hetke and S.C. Bledsoe, Jr., IEEE Transactions of Biomedical Engineering, vol. 44, No. 8, pp. 760–769 (Aug. 1997).
"A Silicon Probe with Integrated Microheaters for Thermal Marking and Monitoring of Neural Tissue", J. Chen and K.D. Wise, IEEE Transactions of Biomedical Engineering, vol. 44, No. 8, pp. 770–774 (Aug. 1997).

* cited by examiner

Primary Examiner—Mark Bockelman
(74) Attorney, Agent, or Firm—Baker Botts L.L.P.

(57) ABSTRACT

An improved probing device includes: an elongated, substantially cylindrical flexible fiber having a non-conducting outer surface; one or more circuits disposed on the outer surface of the fiber for simultaneously providing an electrical signal path to and from a plurality of locations, each of the circuits comprising a non-planar integrated circuit extending lengthwise along the outer surface of the fiber; and an insulating layer substantially disposed over the electrical circuits and around the outer surface of the fiber, the insulating layer having a plurality of openings through which selected portions of the electrical circuits are exposed to the locations. Such a probing device when adapted as a neural probe is especially useful for conducting deep brain measurement and stimulation.

36 Claims, 5 Drawing Sheets

FLEXIBLE PROBING DEVICE AND METHODS FOR MANUFACTURING THE SAME

BACKGROUND OF INVENTION

FIELD OF THE INVENTION

The present invention relates in general to the field of signal monitoring and delivery. More particularly, the present invention relates to medical monitoring and treatment devices and their methods of manufacture.

BACKGROUND OF THE INVENTION

Presently known devices for monitoring conditions within a living body, such as neural probes and other catheter devices, are often limited by the number of available terminal or recording sites and are difficult to handle and insert into proper position within the body. For example, commercially available single-wire "hybrid" neural probes, such as the Activa® device available from Medtronic, Inc., are costly and limited to a relatively few number of recording sites. Such "hybrid" devices have separately manufactured circuit components, as opposed to integrated circuit components that are manufactured as a monolithic structure. It is well known in the art, however, that integrated circuits approach typically offer greater functionality, smaller size and lower cost. See W. Koller et al., "High-frequency Unilateral Thalamic Stimulation in the Treatment of Essential and Parkinsonian Tremor," Annals of Neurology, vol. 42, no. 3, pp. 292–299 (September 1997).

Other known devices suitable for neural probes include multiple recording sites having planar integrated circuits formed by conventional planar silicon micro-fabrication techniques. See K. Najafi, K. D. Wise and T. Mochizuki, "A High Yield IC Compatible Multichannel Recording Array," IEEE Transactions on Electron Devices, vol. ED-32, no. 7, pp. 1206–1211 (July 1985); K. Najafi and K. D. Wise, "An Multi-electrode Array with on Chip Signal Processing," IEEE Journal of Solid State Circuits, vol. 21, no. 6, pp. 1035–1044 (December 1986); J. Ji, and K. D. Wise, "An Implantable CMOS Circuit Interface for Multiplexed Microelectrode Recording Arrays," IEEE Journal of Solid State Circuits, vol. 27, no. 3, pp. 433–443 (March 1992); A. C. Hoogerwerf, and K. D. Wise, "A Three Dimensional Microelectrode Array For Chronic Neural Recording," IEEE Transactions of Biomedical Engineering, vol. 41, no. 12, pp. 1136–1146 (December 1994); J. Chen, K. D. Wise, J. F. Hetke, and S. C. Bledsoe, Jr., "A Multichannel Neural Probe for Selective Chemical Delivery at the Cellular Level," IEEE Transactions of Biomedical Engineering, vol. 44, no. 8, pp. 760–769 (August 1997); J. Chen and K. D. Wise, "A Silicon Probe with Integrated Microheaters for Thermal Marking and Monitoring of Neural Tissue," IEEE Transactions of Biomedical Engineering, vol. 44, no. 8, pp. 770–774 (August 1997). Although such devices have been shown to be useful for cortical recording and stimulation, devices having planar circuits formed by conventional integrated circuit fabrication techniques are rigid and as such are difficult to handle during insertion. Conventional neural probes, for example, having rigid planar integrated circuits are therefore ill-suited for deep brain applications and other medical uses.

SUMMARY OF THE INVENTION

Therefore, a principal object of the present invention is to provide a flexible probing device having multiple terminal sites that is particularly useful for various medical applications including deep brain measurement and stimulation.

Another object of the present invention is to provide a method of manufacturing a flexible probing device having multiple terminal sites comprised of multiple non-planar integrated circuits.

Yet another object of the present invention is to provide a flexible probing device having a substantially increased number of terminal sites for performing localized and simultaneous monitoring and mapping of many electrical signals.

Yet another object of the present invention is to provide a flexible probing device that allows for the more effective monitoring and treatment of neurological and other medical disorders.

Still another object of the present invention is to provide a flexible probing device having multiple terminals wherein each terminal is used for both simultaneously monitoring and providing treatment functions.

Yet another object of the present invention is to provide a substantially cylindrical probing device wherein recording of neural or other biological signals is performed over a surface area extending over substantially $2\pi$ radians.

In accordance with the present invention, a probing device is provided having: an elongated, substantially cylindrical flexible fiber having a non-conducting outer surface; one or more electrical circuits disposed on the outer surface of the fiber each for simultaneously providing an electrical signal path to and from one or more corresponding locations, each of the electrical circuits comprising a non-planar integrated circuit extending lengthwise along the outer surface of the fiber; and an insulating layer substantially disposed over the electrical circuits and around the outer surface of the fiber, the insulating layer having one or more openings through which selected portions of the electrical circuits are exposed to the locations. The exposed electrical circuits on the outer surface of the fiber can be passive or active circuits for conveying electrical signals to and from the corresponding locations.

In another embodiment of the present invention, a medical probe includes: an elongated, substantially cylindrical flexible fiber having a non-conducting outer surface; a plurality of electrical circuits disposed on the outer surface of the fiber each for simultaneously providing an electrical signal path between a plurality of corporeal regions and one or more extracorporeal sites, each of the electrical circuits comprising a non-planar integrated circuit extending lengthwise along the outer surface of the fiber; and an insulating layer substantially disposed over the electrical circuits and around the outer surface of the fiber, the insulating layer having a plurality of openings through which selected portions of the electrical circuits are exposed to the corporeal regions.

In yet another preferred embodiment of the present invention, the medical probe of the present invention is adapted to function as a neural probe for monitoring neural activities and providing stimulation treatment. The neural probe, which is especially suited for deep brain measurement and stimulation, includes: an elongated, substantially cylindrical flexible fiber having a non-conducting outer surface; a plurality of electrical circuits disposed on the outer surface of the fiber each for simultaneously providing an electrical signal path between a plurality of neural regions and one or more extracorporeal sites, each of the electrical circuits comprising a non-planar integrated circuit formed on the outer surface of the fiber; and an insulating layer disposed over the electrical circuits and around the outer surface of the fiber, the insulating layer having a plurality of openings through which selected portions of the electrical circuits are exposed to the neural regions. Advantageously, the terminals of the neural probe can be used for recording neural activity and/or providing stimulation treatment to localized areas of the brain. Stimulation treatment may include, for example, thalamic stimulation for pain and tremor, sub-thalamic stimulation for hemiballismus and Parkinson's disease, pallidal stimulation for dysitonia, and other stimulation treatments for various phychiatric disorders.

In another aspect of the present invention, a method is provided for manufacturing a probing device having multiple non-planar integrated circuits disposed along the outer surface of an elongated, substantially cylindrical flexible fiber. The method includes the steps of: applying a first resist layer onto the outer surface of the fiber; patterning the first resist layer to form a pattern of multiple non-planar integrated circuits disposed along the outer surface of the fiber; depositing one or more material layers onto the patterned outer surface of the fiber to form the circuits; removing remaining portions of the first resist layer; depositing one or more insulating layers on the fiber; applying onto the insulating layers a second resist layer; patterning the second resist layer to form an openings pattern in the second resist layer; transferring the openings pattern onto the insulating layers to form a plurality of openings through which the circuits are exposed; and removing remaining portions of the second resist layer. The material layers can be, for example, metal or semiconductor layers. Preferably, the patterning of the first and second resist layers is performed using conventional electron or ion beam lithography.

In accordance with another preferred embodiment of the present invention, a method of manufacturing a probing device is provided having the steps of: depositing one or more material layers onto the outer surface of an elongated, substantially cylindrical flexible fiber; applying a first resist layer onto the deposited material layers; patterning the first resist layer to form a pattern of multiple non-planar integrated circuits disposed along the outer surface of the fiber; removing exposed portions of the material layers; removing remaining portions of the first resist layer; depositing one or more insulating layers on the remaining material layers and fiber; applying a second resist layer onto the deposited insulating layers; patterning the second resist layer to form an openings pattern in the second resist layer; transferring the openings pattern into the one or more insulating layers to form a plurality of openings through which the circuits are exposed; and removing remaining portions of the second resist layer. Again, preferably, the patterning of the first and second resist layers is performed using conventional electron or ion beam lithography.

By forming non-planar integrated circuits on the outer surface of the flexible fiber, the number of terminals, i.e., recording and/or stimulation sites, can be dramatically increased to upwards of 100 thus improving the usefulness and reliability of the probe while reducing manufacturing costs.

Further objects, features and advantages of the invention will become apparent from the following detailed description taken in conjunction with the accompanying figures showing illustrative embodiments of the invention.

BRIEF DESCRIPTION OF THE DRAWINGS

For a complete understanding of the present invention and the advantages thereof, reference is now made to the following description taken in conjunction with the accompanying drawings in which like reference numbers indicate like features and wherein.

DETAILED DESCRIPTION OF THE PREFERRED EMBODIMENTS

Figure 1:
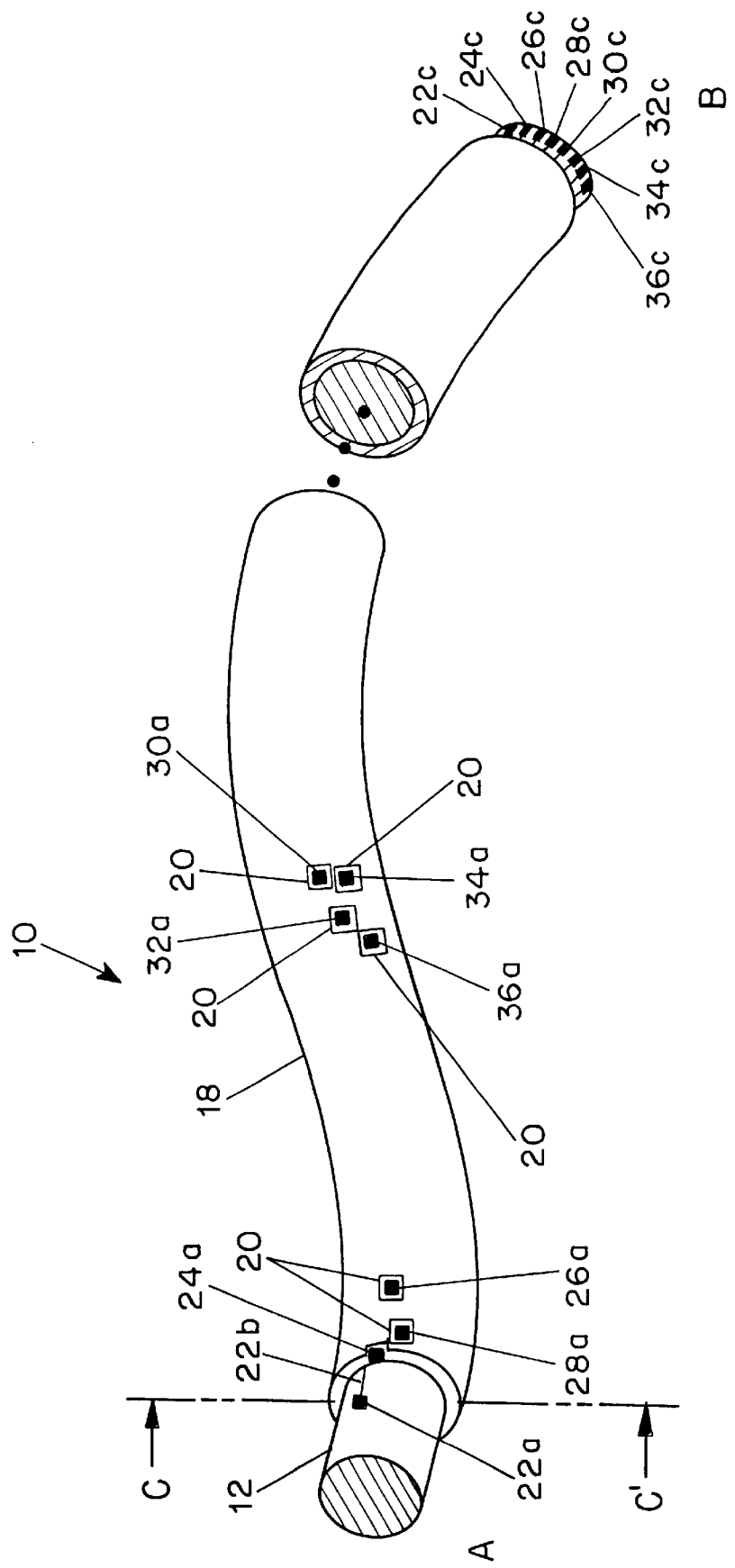
FIG. 1 is a sectional view of a segment of a probing device with an outer insulating layer according to a preferred embodiment of the present invention.

FIG. 1 is a sectional view of a segment of a probing device 10 according to a preferred embodiment of the present invention. The probe 10 includes a substantially cylindrical, electrically isolated flexible fiber 12 having an outer surface covered by an insulating layer 18 having openings 20 formed therein. The fiber 12 is preferably a long symmetrical optical fiber made of, for example, pure quartz or quartz coated in acrylate. The probe 10 has a distal end A, which is inserted into the body, and a proximal end B for connecting to extracorporeal monitoring or stimulation equipment. As shown with further reference to FIG. 2, which is the same view as FIG. 1 but without the insulating layer 18, the probe 10 further includes a plurality of electrical circuits 22, 24, 26, 28, 30, 32, 34 and 36 disposed on the outer surface of the fiber 12 beneath the insulating layer 18 for simultaneously providing an electrical signal path between a plurality of corporeal regions exposed by openings 20, for example, various locations within the brain, and one or more extracorporeal sites, i.e., a monitoring device, stimulation device, connector or otherwise located at an external site. FIG. 3, which is a cross-sectional view C–C' corresponding to FIG. 1, further shows the arrangement of the circuit 22 and opening 20 on the fiber 12, which is the same for circuits 24, 26, 28, 30, 32, 34 and 36.

Figure 2:
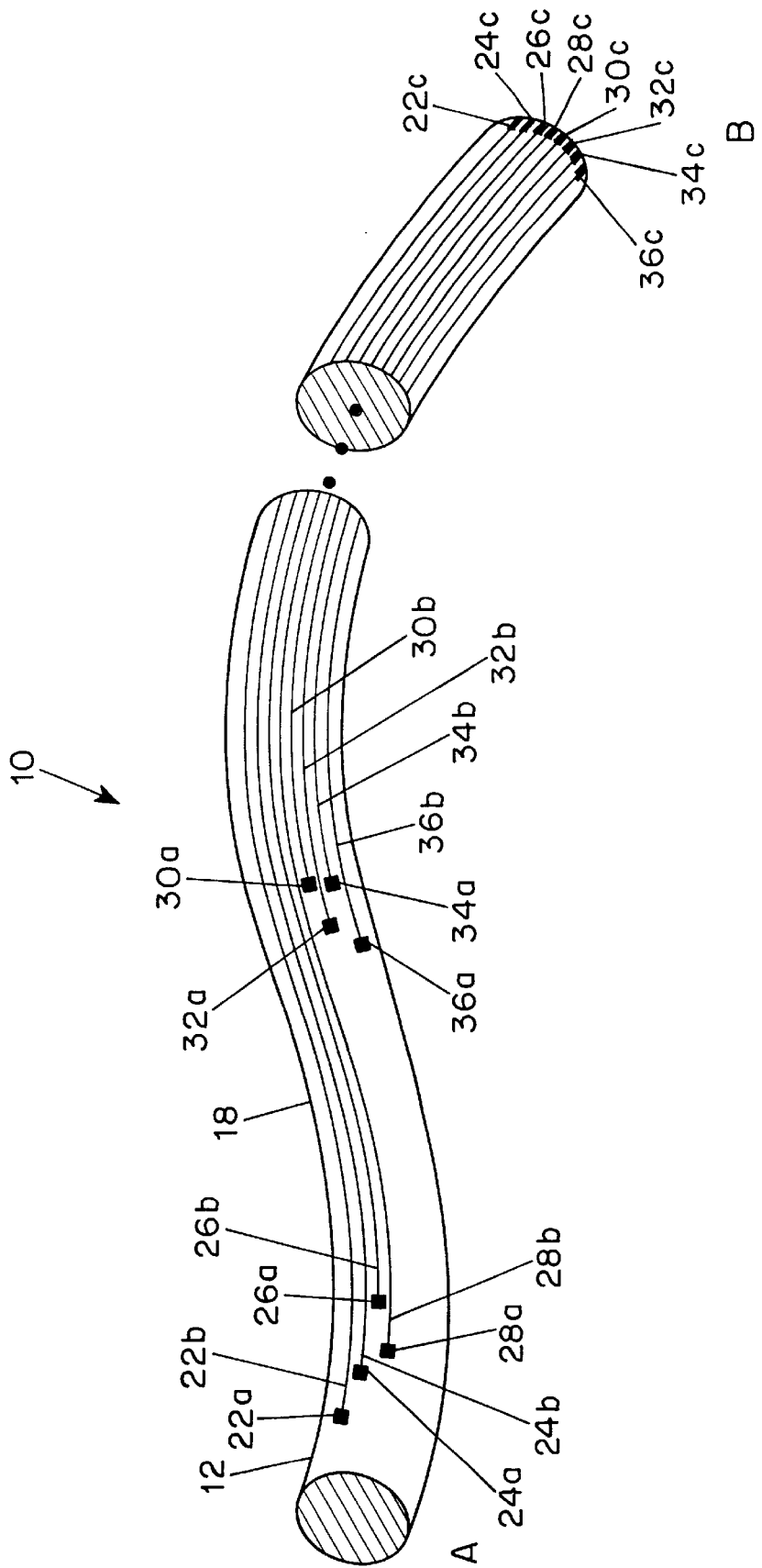
FIG. 2 is a sectional view of the probing device of FIG. 1 without the outer insulating layer.
Figure 3:
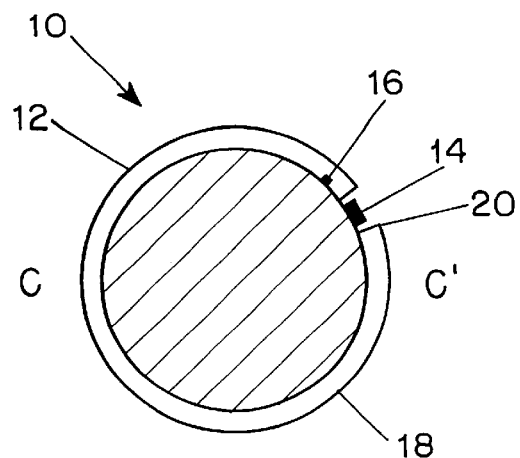
FIG. 3 is a cross-sectional view of the probing device taken along the line C–C' of FIG. 1.

Each of the circuits of FIGS. 1–3 includes non-planar integrated circuit elements, 22a–22c through 36a–36c, extending lengthwise from the distal end A to the proximal end B along the outer surface of the fiber 12. By "distal end A" it is understood to include any point along the fibers longitudinally displaced from the proximal or external end B.

For the purposes of the present application, a "non-planar integrated circuit" is defined generally an integrated circuit formed on a non-planar surface using known integrated circuit fabrication technologies. "Integrated circuit" refers to a combination of interconnected circuit elements formed on a substrate such as the fiber material described herein. "Circuit elements" broadly includes any passive circuit elements, such as electrodes and conducting wires, as well as active circuit elements such as transistors, sensors, converters, etc., formed using known integrated circuit technologies.

Referring again to the embodiment of FIGS. 1–3, each of the circuits includes a non-planar first circuit element, e.g., circuit elements 22a, 24a, 26a, 28a, 30a, 32a, 34a, and 36a, disposed on the outer surface of the fiber 12 between its distal and proximal ends, and within a corresponding one of the openings 20 within the insulating layer 18. Non-planar second circuit elements, e.g., circuit elements 22c, 24c, 26c, 28c, 30c, 32c, 34c, and 36c, corresponding to the first circuit elements are disposed on the outer surface of the fiber 12 adjacent its proximal end B. Each of the corresponding first and second circuit element pairs 22a/22c, 24a/24c, 26a/26c, etc., are respectively connected by non-planar conducting strands 22b, 24b, 26b, 28b, 30b, 32b, 34b, and 36b, which are arranged lengthwise along the outer surface of the fiber 12 for conveying electrical signals to and from the corresponding first and second circuit elements of the integrated circuit.

The probe 10 therefore comprises a plurality of circuits including circuit elements that are simultaneously exposed to corresponding regions to be monitored and/or stimulated. In the neural probe embodiment, each of such exposed circuit elements, which is nominally a 30 $\mu$m×30 $\mu$m conducting pad, is connected via a conducting strand to a corresponding second circuit element 22c, 24c, 26c, etc., which is nominally an exposed 75 $\mu$m×75 $\mu$m bonding pad for connecting the probe to external monitoring or stimulation equipment or the like. The exposed circuit elements can also be active circuit elements, such as sensors for sensing temperature, blood flow, etc., actuators, analog-to-digital converters and preamplifiers. The active circuit elements can be semiconductor devices formed using known integrated circuit fabrication techniques.

Figure 4:
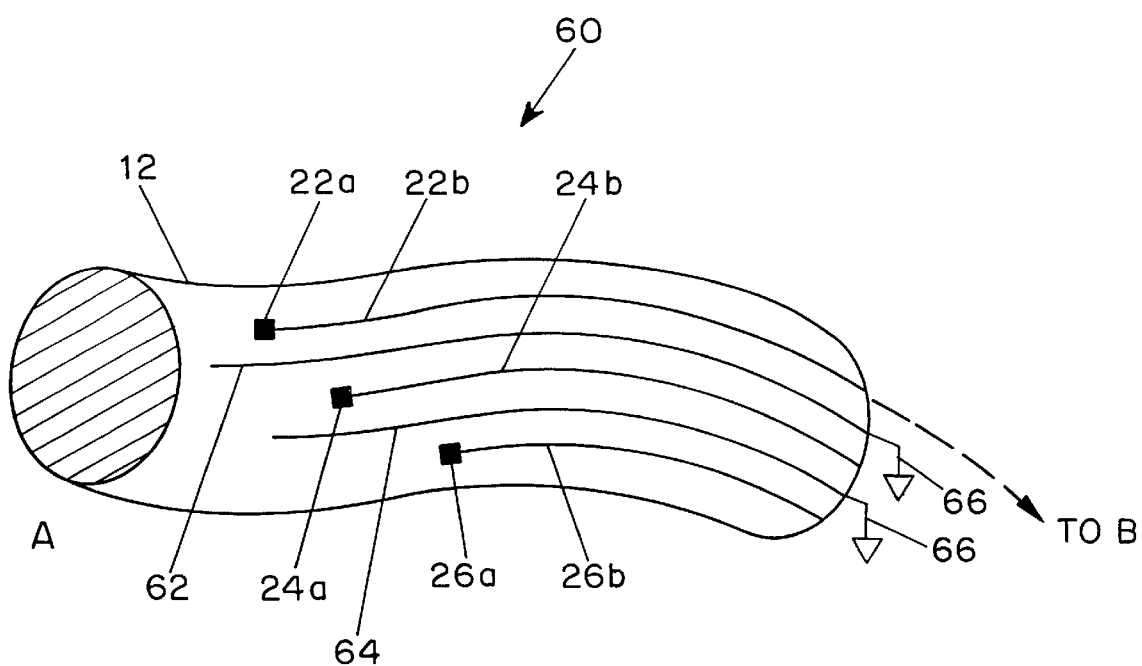
FIG. 4 is a sectional view of the probing device of FIG. 1 with conducting ground traces.

Each of the conducting strands 22b, 24b, 26b, etc., connecting the first and second circuit elements are required to be wide enough so as to minimize the electrical resistance of the strand. For this reason, the nominal width for a long interconnecting strand is selected to be approximately 1.5 $\mu$m. In addition, in order to minimize interference or "crosstalk" between adjacent or nearby strands, the strands are placed at least 5 $\mu$m apart. Further as shown in FIG. 4, grounded conducting traces, e.g., traces 62 and 64, can be disposed between the conducting strands to further reduce crosstalk without increasing the strand spacing or decreasing the number of recording/stimulating sites.

As such, a medical probe having 133 30 $\mu$m×30 $\mu$m recording/stimulating sites with corresponding 1.5 $\mu$m thick conducting strands spaced 5 $\mu$m apart can be manufactured on a standard 0.25 mm diameter optical fiber. For a 1.0 mm diameter fiber, which is smaller than conventional devices, a probe according to the present invention can be designed to have over 500 recording/stimulating sites.

The above-described probing device of FIGS. 1–4 can thus be arranged and constructed, for example, as a neural probe or other medical probing device having multiple circuit elements for simultaneously monitoring and/or treating a plurality of locations or regions within the body. When used as a neural probe, the probing device of the present invention enables simultaneously conveying of electrical signals to and from a plurality of neural regions at one time.

Because of its flexible construction and numerous terminal sites, the probe 10, when adapted to be used as a neural probe, is especially useful for deep brain monitoring and for providing stimulation treatment to localized areas of the brain. Stimulation treatment may include, for example, thalamic stimulation for pain and tremor, sub-thalamic stimulation for hemiballismus and Parkinson's disease, pallidal stimulation for dysitonia, and other stimulation treatments for various phychiatric disorders.

Figure 5:
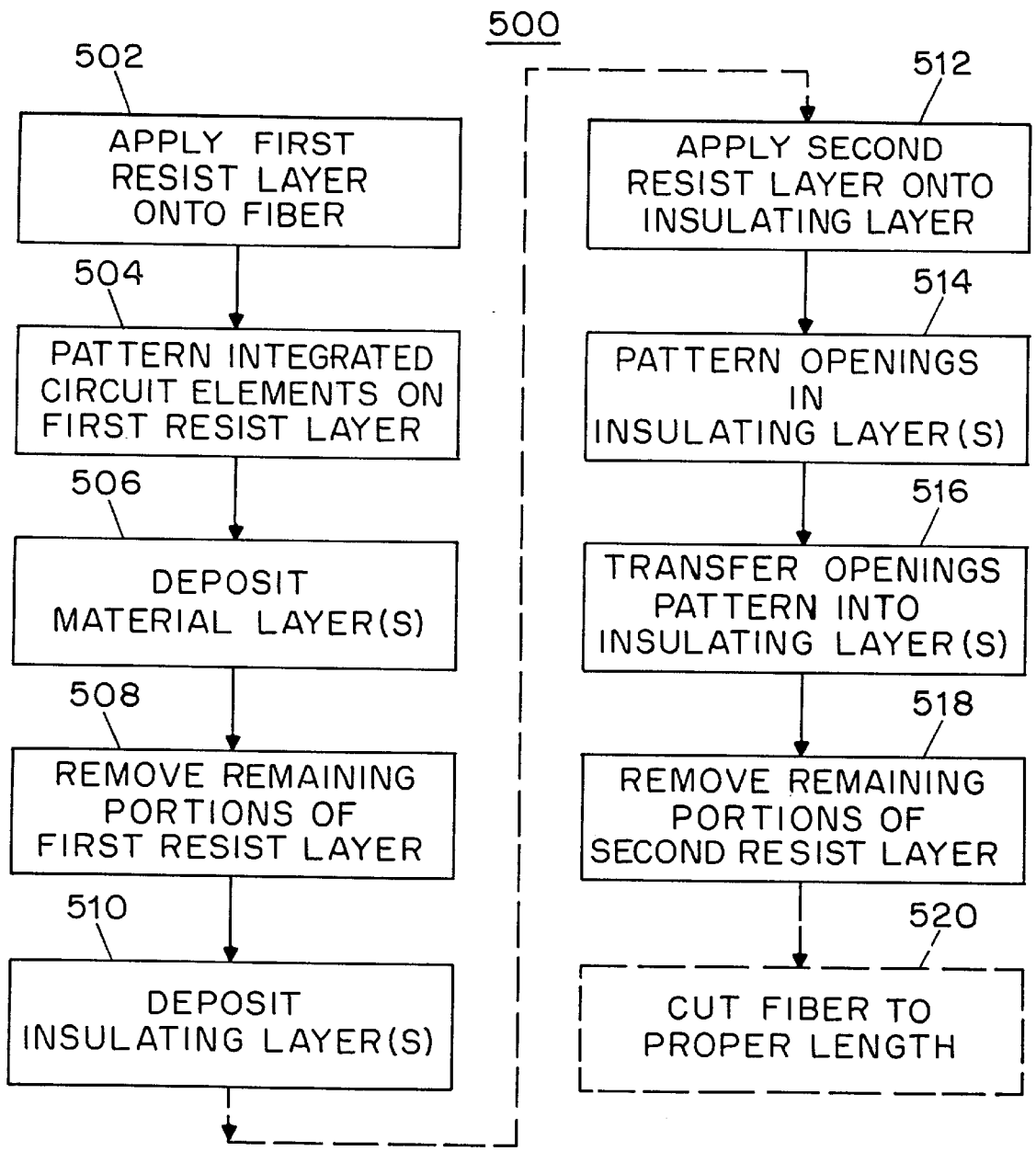
FIG. 5 is a flow diagram of a preferred method of manufacturing the probing device of FIG. 1.

FIG. 5 is a flow diagram showing a preferred method of manufacturing a flexible probing device having multiple non-planar integrated circuits as shown in FIGS. 1–4. The method includes the steps of: applying a first resist layer onto the outer surface of an elongated, substantially cylindrical flexible fiber (Step 502); patterning the first resist layer, using for example conventional electron or ion beam lithography, to form a pattern of multiple non-planar integrated circuits disposed along the outer surface of the fiber (Step 504); depositing one or more material layers, e.g. conductors, semiconductors, etc., onto the patterned outer surface of the fiber to form the circuits (Step 506); removing remaining portions of the first resist layer (Step 508); depositing one or more insulating layers on the circuits and outer surface of the fiber (Step 510); applying onto the insulated fiber a second resist layer (Step 512); patterning the second resist layer using conventional electron or ion beam lithography to form an openings pattern in the second resist layer (Step 514); transferring the openings pattern into the insulating layers to form a plurality of openings in through which the circuits are exposed (Step 516); and removing remaining portions of the second resist layer (Step 518). The fiber is then cut to size as required (Step 520).

As shown in FIG. 5, a first resist layer of ion beam sensitive material is applied or "spun" onto the outer surface of an optical fiber (Step 502). Application of the first resist per Step 502 can be performed by holding the fiber at one end and spinning the loose end like a whip. The centrifugal forces generated are comparable to those generated on a spinning planar surface. Alternatively, the fiber is held in tension at both ends and the resist is spun on by rotating the fiber about its longitudinal axis, or the fiber can be pulled through a resist solution and then through a hot zone to drive off excess the resist.

The resist thickness can be measured by cross sectioning and examining the actual fiber through a scanning electron or transmission electron microscope. Alternatively, the resist thickness can be measured by exposing the coated fiber to a focused ion beam. The depth of penetration of ions is well defined as a function of ion species and energy. Thus, a focused ion beam can be used to create patterns at various energies and therefore at precise penetration depths. Measuring of the penetration depths thus allows for the calibration of the resist spinning process.

Next, the first resist layer is patterned using focused ion beam lithography to define the required circuit elements, such as the conducting strands 22b, 24b, 26b, etc., of FIGS. 1–4 (Step 504). The first resist layer, however, can be patterned using other conventional lithography techniques such as electron beam lithography. In addition, alignment marks may also be patterned on the first resist layer to aid in subsequent lithography of fiber surface structures. Preferably, these alignment marks are placed on the opposing ends of the fiber.

Referring again to FIG. 5, the non-planar integrated circuits are patterned using modified integrated circuit fabrication techniques used to fabricate planar circuits. As can be appreciated by those skilled in the art, conventional integrated circuit fabrication techniques are limited to planar devices because the depth of focus of conventional lithography equipment is limited. For example, with integrated circuit fabrication utilizing optical lithography, patterning of non-planar surfaces is extremely difficult due to the depth of focus of a conventional optical stepper, which is typically about one-fourth to one-eighth the resolution of the optical stepper. As such, a 1 $\mu$m resolution optical stepper can stay in focus only over a depth of approximately 0.25 $\mu$m. Although focused ion and electron beam lithography techniques provide better alternatives, throughput limitations associated with these techniques usually make them unsuitable for high-volume commercial applications. Thus, it is desirable to use ion or electron beam lithography that both have a large depth of focus for the purpose of the present invention.

For low-to-medium volume applications such as required for mass-producing the probing devices of FIGS. 1–4, focused electron and ion beam lithography has been shown by the present inventors to be viable manufacturing alternatives since the throughput limitations are not as critical. Thus, focused electron and ion beam lithography may be effectively used to form the non-planar integrated circuits shown in FIGS. 1–4.

Figure 6:
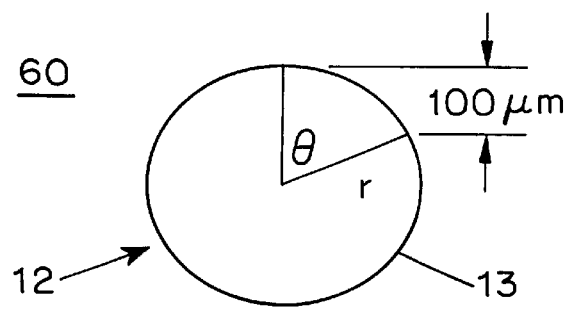
FIG. 6 is a diagram illustrating an example of the depth of focus limitations of the preferred method of FIG. 5.

In a preferred method of the present invention, a focused ion beam system such as the Nanofab 150 available from Nanofab, Inc. is used to form non-planar integrated circuits on the fiber. The Nanofab 150 is preferred in that it is characterized by a depth of focus of 100 μm and beam diameter variation of 20%. Thus, for a fiber 12 having a standard diameter of 0.25 mm (radius r=125 μm) as shown in FIG. 6, the Nanofab 150 can be used to pattern the outer surface 13 up to +/−78 degrees (angle θ) from the vertical 32. Limiting the patterning to +/−45 degrees is however more practical since the glancing incidence of the beam beyond 45 degrees tends to complicate the pattern transfer processes.

In any event, by using a conventional focused ion beam system such as the above-described Nanofab 150, the circuit elements can be patterned completely around the outer surface of the fiber 12 by performing, for example, four 90 degree rotations of the fiber 12. Further, "stitching" or connecting of adjacent circuits along the fiber can be performed using a standard laser interferometrically controlled stage. The rotation of the fiber can be readily achieved by using a suitable pallet that rides on a laser stage.

Referring again to FIG. 5, layers of platinum (Pt) and iridium (Ir) metal are then deposited, using evaporation, sputtering or other suitable method, onto the fiber to form the non-planar circuits (Step 506). Other suitable metals include gold (Au), chromium (Cr) and palladium (Pd). If bonding pads are to be provided, layers of Cr or Au are preferred and similarly deposited onto the corresponding regions of the flexible fiber. Uniform deposition can be further achieved by slowly rotating the fiber as described above with respect to the first resist layer. After exposure to the focused ion beam and assuming a positive resist is used, the exposed regions of the resist layer are removed in a developing solution (Step 508). If a negative resist is used, the unexposed regions of the first resist layer are removed. If the bonding pads are to be provided, the bonding pads are similarly patterned and developed at one end of the fiber. Upon completion of Step 508, the metal left on the surface of the fiber where the resist was patterned defines the non-planar circuits and any patterned alignment marks.

Next, one or more insulating layers are deposited on the fiber preferably by applying a layer of spun-on glass or polyimide (Step 510). Alternatively, silicon dioxide can be sputtered onto the fiber, assuming the fiber can withstand a temperature of 100° C. A second resist layer sensitive to an ion beam, preferably a positive resist, is then spun onto the fiber (Step 512) as described above with respect to the first resist layer. If alignment marks or bonding pads are formed, any resist and/or portions of the insulator layer covering the alignment marks and/or bonding pads are stripped away.

A second patterning step is then performed using focused ion beam lithography to pattern openings in the second resist layer aligned with the portions of the integrated circuits to be exposed to the corporeal regions to be monitored and/or stimulated (Step 514). This step can also be performed using other conventional lithography techniques such as electron beam lithography. The second patterning step can also be performed to expose the bonding pads on the proximal end of the fiber. A subsequent wet chemical or dry reactive ion etch is then performed to transfer the resist openings into the insulating layer(s) (Step 516). The remaining second resist layer is stripped using a strong solvent to expose the outer surface of the insulated fiber with the openings formed therein (Step 518). The fiber is then cut to the appropriate length as required (Step 520). The fabrication cycle according to the method of FIG. 5 is approximately 2 to 3 days.

In addition, computer-aided design (CAD) information specifying the layout of the circuit elements can be used with the above-mentioned Nanofab 150 device. Under computer control, for example, patterns can be written having a placement accuracy of 8 nm by using electronic deflection of the ion beam and precise movement of a laser interferometrically controlled stage. Although the focused ion beam procedure is a serial lithography technique wherein pixels are written one pixel at a time, the relatively coarse feature sizes and simple patterns of the non-planar circuits result in short exposure or patterning times. Using a standard negative ion beam resist, e.g., SAL601, and a 1 μm diameter singly charged boron beam at 100 keV, the total exposure or patterning time for a 3 cm long fiber having 16 rings of recording sites over an 8 mm segment is approximately 8 seconds. The relatively short exposure time makes this technique especially useful for rapid prototyping and refining the probe design. For example, such a system can be used to conveniently vary other design parameters, such as the size of the openings in the insulating layer, so as to refine or "tune" the performance of the medical probe for a particular application.

The method of FIG. 5 can be further extended to other types of fiber materials, other than pure quartz or acrylate coated quartz, for example nylon. Nylon fibers permit the most flexibility, but require relatively low processing temperatures, for example, less than 200°. Pure quartz fibers, on the other hand, are not as flexible but can withstand processing temperatures well over 1000° C. The fiber can be solid or hollow. In addition, polycrystalline silicon can be deposited on a pure quartz fiber at a temperature of 650 ° C. allowing the fabrication of micro-electromechanical sensors and actuators. Further, pure quartz fibers remain flexible even with small diameters such as the 125 μm diameter.

Figure 7:
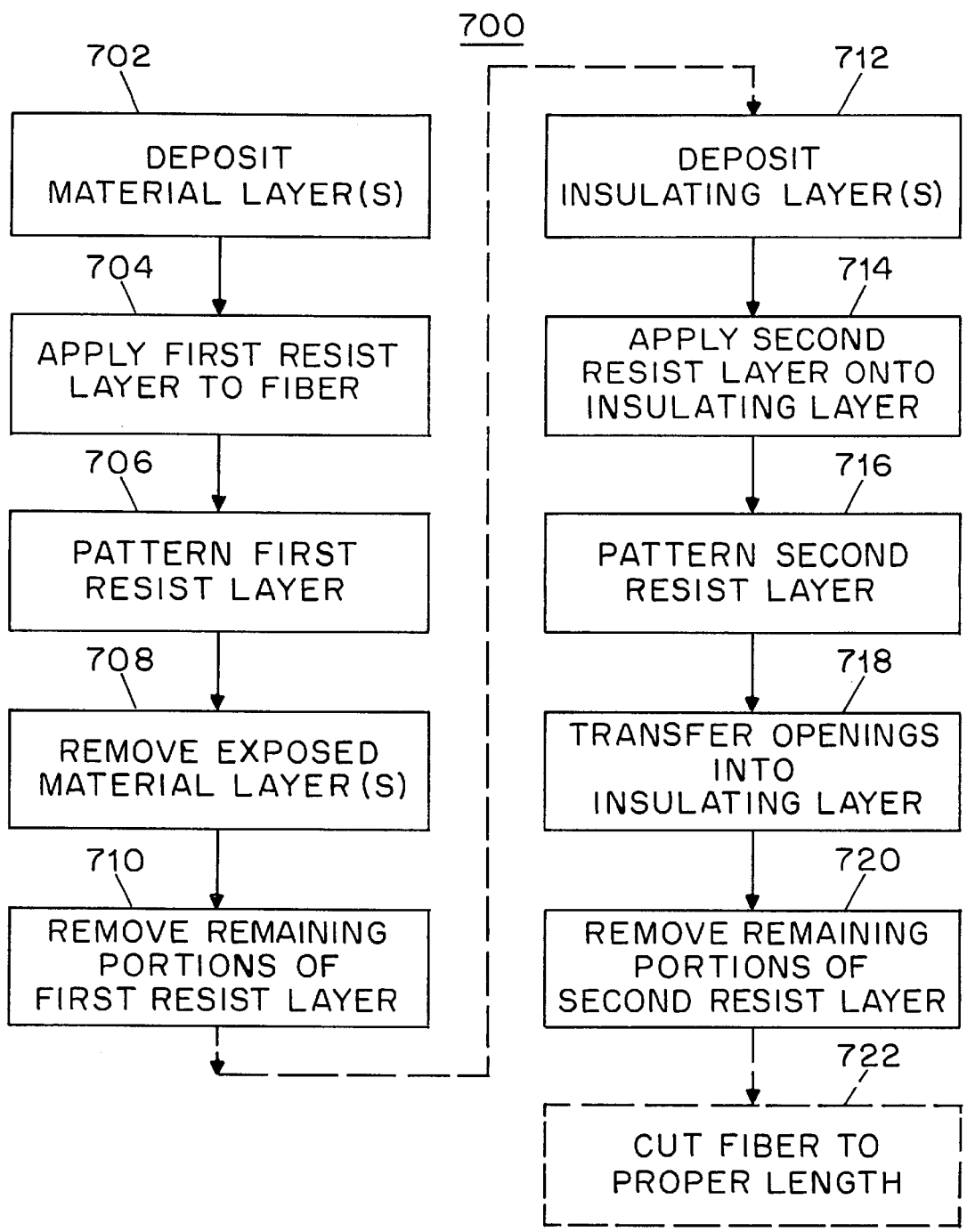
FIG. 7 is a flow diagram of another preferred method of manufacturing the probing device of FIG. 1.

FIG. 7 shows another preferred method of manufacturing the probing device of FIG. 1. The method is similar to the method of FIG. 5, but instead utilizes a negative resist for patterning the circuit elements on a fiber. As shown in FIG. 7, the method includes the steps of: depositing one or more material layers onto the outer surface of an elongated, substantially cylindrical flexible fiber (Step 702); applying onto the deposited material layers a first resist layer (Step 704); patterning the first resist layer to form a pattern of multiple non-planar integrated circuits disposed along the outer surface of the fiber (Step 706); removing exposed portions of the material layers (Step 708); removing remaining portions of the first resist layer (Step 710); depositing one or more insulating layers on the remaining material layers and fiber (Step 712); applying a second resist layer onto the deposited insulating layers (Step 714); patterning the second resist layer to form an openings pattern in the second resist layer (Step 716); transferring the openings pattern into the one or more insulating layers to form a plurality of openings through which the circuits are exposed (Step 718); removing remaining portions of the second resist layer (Step 720); and optionally cutting the fiber to a desired length (Step 722). As with the method of FIG. 500, the patterning steps 706 and 716 can be performed using conventional electron or ion beam lithography techniques used for manufacturing planar integrated circuits.

Thus, numerous catheter based medical treatments may be improved by fabricating sensors, preamplifiers and even analog-to-digital converters utilizing the probe design of the present invention. Such devices, for example, can be located at the distal end of the probe to provide more accurate measurements and effective treatment. Furthermore, the probe design of the present invention can be coupled with a light source and adapted to simultaneously serve as a "light pipe" for allowing visual observation inside the body. Doppler measurements can be used to determine blood flow in the region of the brain where electrical measurements are being made simultaneously so as to correlate neural activity to blood flow. In another embodiment of the present invention, in addition to providing stimulation and recording functionality, micro-channels can be provided within the insulative coating of a neural probe to deliver neuro-chemicals at the cellular level. Suitable micro-valves can further be included in the probe to prevent intermixing between neural fluids and neural chemicals when delivery of neural chemicals is not desired.

Although the present invention has been described in connection with particular embodiments thereof, it is to be understood that such embodiments are susceptible of modification and variation without departing from the scope of the inventive concept as defined by the appended claims.

What is claimed is:

1. A probing device comprising:
   an elongated, substantially cylindrical flexible fiber having a non-conducting outer surface;
   one or more electrical circuits disposed on the outer surface of said fiber each for simultaneously providing an electrical signal path to and from one or more corresponding locations, each of said electrical circuits comprising a non-planar integrated circuit extending lengthwise along the outer surface of said fiber; and
   an insulating layer substantially disposed over said electrical circuits and around the outer surface of said fiber, said insulating layer having one or more openings through which selected portions of said electrical circuits are exposed to the locations.

2. The device according to claim 1, wherein said non-planar integrated circuit comprises:
   a first circuit element disposed on the outer surface of said fiber and within one of said openings in said insulating layer such that said first circuit element is exposed to a corresponding one of said locations;
   a second circuit element disposed on the outer surface of said fiber and displaced longitudinally from said first circuit element;
   a conducting strand connecting said first and second circuit elements along the outer surface of said fiber for conducting electrical signals to and from said first and second circuit elements.

3. The device according to claim 2, wherein said first and second circuit elements comprise conducting pads.

4. The device according to claim 2, wherein said conducting strand has a minimum thickness so as to minimize the electrical resistance of said strand.

5. The device according to claim 2, wherein said device comprises a plurality of conducting strands and each of said conducting strands is spaced apart from adjacent conducting strands by a minimum distance so as to minimize interference between said circuits.

6. The device according to claim 2, wherein said device comprises a plurality of conducting strands, said probing device further comprising conducting ground traces interposed between adjacent pairs of said conducting strands for reducing signal interference on said conducting strands.

7. The device according to claim 1, wherein said non-planar integrated circuit comprises:
   at least one sensor disposed on the outer surface of said fiber and within a corresponding one of said openings in said insulating layer such that said sensor is exposed to a corresponding one of said locations;
   a circuit element disposed on the outer surface of said fiber and displaced longitudinally from said sensor;
   a conducting strand connecting said sensor and said circuit element and arranged lengthwise along the outer surface of said fiber for conducting electrical signals to and from said sensor and said circuit element.

8. The device according to claim 1, wherein said non-planar integrated circuit comprises:
   at least one actuator disposed on the outer surface of said fiber and within a corresponding one of said openings in said insulating layer such that said actuator is exposed to a corresponding one of said locations;
   a circuit element disposed on the outer surface of said fiber and displaced longitudinally from said actuator;
   a conducting strand connecting said actuator and said circuit element and arranged lengthwise along the outer surface of said fiber for conducting electrical signals to and from said actuator and said circuit element.

9. The device according to claim 1, wherein said non-planar integrated circuit comprises:
   at least one semiconductor device disposed on the outer surface of said fiber and within a corresponding one of said openings in said insulating layer such that said semiconductor device is exposed to a corresponding one of said locations;
   a circuit element disposed on the outer surface of said fiber and displaced longitudinally from said semiconductor device;
   a conducting strand connecting said semiconductor device and said circuit element and arranged lengthwise along the outer surface of said fiber for conducting electrical signals to and from said semiconductor device and said circuit element.

10. The device according to claim 1, wherein said non-planar integrated circuit comprises:
    at least one micro-valve for delivering chemical treatments disposed on the outer surface of said fiber and within a corresponding one of said openings in said insulating layer such that said micro-valve is exposed to a corresponding one of said locations;
    a circuit element disposed on the outer surface of said fiber and disposed longitudinally from said micro-valve;
    a conducting strand connecting said micro-valve and said circuit element and arranged lengthwise along the outer surface of said fiber for conducting electrical signals to and from said micro-valve and said circuit element.

11. The device according to claim 1, further comprising one or more micro-channels disposed in said insulating layer for delivering chemical treatments.

12. The device according to claim 1, wherein said fiber is an optical fiber and said device further comprises a light source coupled to said optical fiber for allowing visual observation of said locations.

13. A medical probe comprising:
an elongated, substantially cylindrical flexible fiber having a nonconducting outer surface;
a plurality of electrical circuits disposed on the outer surface of said fiber each for simultaneously providing an electrical signal path between a plurality of corporeal regions and one or more extracorporeal sites, each of said electrical circuits comprising a non-planar integrated circuit extending lengthwise along the outer surface of said fiber; and
an insulating layer substantially disposed over said electrical circuits and around the outer surface of said fiber, said insulating layer having a plurality of openings through which selected portions of said electrical circuits are exposed to the corporeal regions.

14. The medical probe according to claim 13, wherein said non-planar integrated circuit comprises:
a first circuit element disposed on the outer surface of said fiber and within a corresponding one of said openings in said insulating layer such that said first circuit element is exposed to a corresponding one of said corporeal regions;
a second circuit element disposed on the outer surface of said fiber and displaced longitudinally from said first circuit element;
a conducting strand connecting said first and second circuit elements and arranged lengthwise along the outer surface of said fiber for conducting electrical signals to and from said first and second circuit elements.

15. The medical probe according to claim 14, wherein said first and second circuit elements are conducting pads.

16. The medical probe according to claim 14, wherein said probe comprises a plurality of conducting strands and each conducting strand has a minimum thickness so as to minimize the electrical resistance of said strand.

17. The medical probe according to claim 14, wherein said probe comprises a plurality of conducting strands, and each of said conducting strands is spaced apart from adjacent conducting strands by a minimum distance so as to minimize interference between said circuits.

18. The medical probe according to claim 14, wherein said probe comprises a plurality of conducting strands, said probe further comprising conducting ground traces interposed between adjacent pairs of said conducting strands for reducing signal interference on said conducting strands.

19. The medical probe according to claim 13, wherein said non-planar integrated circuit comprises:
at least one sensor disposed on the outer surface of said fiber and within a corresponding one of said openings in said insulating layer such that said sensor is exposed to a corresponding one of said corporeal regions;
a circuit element disposed on the outer surface of said fiber and displaced longitudinally from said sensor;
a conducting strand connecting said sensor and said circuit element and arranged lengthwise along the outer surface of said fiber for conducting electrical signals to and from said sensor and said circuit element.

20. The medical probe according to claim 13, wherein said non-planar integrated circuit comprises:
at least one actuator disposed on the outer surface of said fiber and within a corresponding one of said openings in said insulating layer such that said actuator is exposed to a corresponding one of said corporeal regions;
a circuit element disposed on the outer surface of said fiber and displaced longitudinally from said actuator;
a conducting strand connecting said actuator and said circuit element and arranged lengthwise along the outer surface of said fiber for conducting electrical signals to and from said actuator and said circuit element.

21. The medical probe according to claim 13, wherein said non-planar integrated circuit comprises:
at least one semiconductor device disposed on the outer surface of said fiber and within a corresponding one of said openings in said insulating layer such that said semiconductor device is exposed to a corresponding one of said corporeal regions;
a circuit element disposed on the outer surface of said fiber and displaced longitudinally from said semiconductor device;
a conducting strand connecting said semiconductor device and said circuit element and arranged lengthwise along the outer surface of said fiber for conducting electrical signals to and from said semiconductor device and said circuit element.

22. The medical probe according to claim 13, wherein said non-planar integrated circuit comprises:
at least one micro-valve for delivering chemical treatments disposed on the outer surface of said fiber and within a corresponding one of said openings in said insulating layer such that said micro-valve is exposed to a corresponding one of said corporeal regions;
a circuit element disposed on the outer surface of said fiber and displaced longitudinally from said micro-valve;
a conducting strand connecting said micro-valve and said circuit element and arranged lengthwise along the outer surface of said fiber for conducting electrical signals to and from said micro-valve and said circuit element.

23. The medical probe according to claim 13, further comprising one or more micro-channels disposed in said insulating layer for delivering chemical treatments.

24. The medical probe according to claim 13, wherein said fiber is an optical fiber and said device further comprises a light source coupled to said optical fiber for allowing visual observation of said locations.

25. A neural probe comprising:
an elongated, substantially cylindrical flexible fiber having a conducting outer surface;
a plurality of electrical circuits disposed on the outer surface of said fiber each for simultaneously providing an electrical signal path between a plurality of neural regions and one or more extracorporeal sites, each of said electrical circuits comprising a non-planar integrated circuit formed on the outer surface of said fiber; and
an insulating layer substantially disposed over said electrical circuits and around the outer surface of said fiber, said insulating layer having a plurality of openings through which selected portions of said electrical circuits are exposed to the neural regions.

26. The neural probe according to claim 25, wherein said non-planar integrated circuit comprises:
a first circuit element disposed on the outer surface of said fiber and within one of said openings in said insulating layer such that said first circuit element is exposed to a corresponding one of said corporeal regions;
a second circuit element disposed on the outer surface of said fiber and displaced longitudinally from said first circuit element;

a conducting strand connecting said first and second circuit elements and arranged lengthwise along the outer surface of said fiber for conducting electrical signals to and from said first and second circuit elements.

27. The neural probe according to claim 26, wherein said first and second circuit elements are conducting pads.

28. The neural probe according to claim 26, wherein said conducting strand has a minimum thickness so as to minimize the electrical resistance of said strand.

29. The neural probe according to claim 26, wherein said probe comprises a plurality of conducting strands, and each of said conducting strands is spaced apart from adjacent conducting strands by a minimum distance so as to minimize interference of said circuits.

30. The neural probe according to claim 29, wherein said fiber is an optical fiber and said device further comprises a light source coupled to said optical fiber for allowing visual observation of said locations.

31. The neural probe according to claim 26, wherein said probe comprises a plurality of conducting strands, said probe further comprising conducting ground traces interposed between said conducting strands for reducing signal interference on said conducting strands.

32. The neural probe according to claim 25, wherein said non-planar integrated circuit comprises:

at least one sensor disposed on the outer surface of said fiber and within a corresponding one of said openings in said insulating layer such that said sensor is exposed to a corresponding one of said neural regions;

a circuit element disposed on the outer surface of said fiber and displaced longitudinally from said sensor;

a conducting strand connecting said sensor and said circuit element and arranged lengthwise along the outer surface of said fiber for conducting electrical signals to and from said sensor and said circuit element.

33. The neural probe according to claim 25, wherein said non-planar integrated circuit comprises:

at least one actuator disposed on the outer surface of said fiber and within a corresponding one of said openings in said insulating layer such that said actuator is exposed to a corresponding one of said neural regions;

a circuit element disposed on the outer surface of said fiber and displaced longitudinally from said actuator;

a conducting strand connecting said actuator and said circuit element and arranged lengthwise along the outer surface of said fiber for conducting electrical signals to and from said actuator and circuit element.

34. The neural probe according to claim 25, wherein said non-planar integrated circuit comprises:

at least one semiconductor device disposed on the outer surface of said fiber and within a corresponding one of said openings in said insulating layer such that said semiconductor device is exposed to a corresponding one of said neural regions;

a circuit element disposed on the outer surface of said fiber and displaced longitudinally from said semiconductor device;

a conducting strand connecting said semiconductor device and said circuit element and arranged lengthwise along the outer surface of said fiber for conducting electrical signals to and from said semiconductor device and circuit element.

35. The neural probe according to claim 25, wherein said non-planar integrated circuit comprises:

at least one micro-valve for delivering chemical treatments disposed on the outer surface of said fiber and within a corresponding one of said openings in said insulating layer such that said micro-valve is exposed to a corresponding one of said neural regions;

a circuit element disposed on the outer surface of said fiber and displaced longitudinally from said micro-valve;

a conducting strand connecting said micro-valve and said circuit element and arranged lengthwise along the outer surface of said fiber for conducting electrical signals to and from said micro-valve and circuit element.

36. The neural probe according to claim 25, further comprising one or more micro-channels disposed in said insulating layer for delivering chemical treatments.

* * * * *

UNITED STATES PATENT AND TRADEMARK OFFICE
CERTIFICATE OF CORRECTION

PATENT NO. : 6,304,784 B1
DATED : October 16, 2001
INVENTOR(S) : Allee et al.

It is certified that error appears in the above-identified patent and that said Letters Patent is hereby corrected as shown below:

Column 1,
Line 37, "An" should read -- An Implantable --

Column 3,
Line 10, "phychiatric" should read -- psychiatric --

Column 5,
Line 65, "phychiatric" should read -- psychiatric --

Column 6,
Line 31, "excess the" should read -- the excess --

Column 9,
Line 55, "element;" should read -- element; and --

Column 10,
Line 16, "sensor;" should read -- sensor; and --
Line 28, "actuator;" should read -- actuator; and --
Line 42, "device;" should read -- device; and --
Line 58, "valve;" should read -- valve; and --

Column 11,
Line 26, "element;" should read -- element; and --
Line 55, "sensor;" should read -- sensor; and --

Column 12,
Line 2, "actuator;" should read -- actuator; and --
Line 16, "device;" should read -- device; and --
Line 31, "valve;" should read -- valve; and --
Line 67, "element;" should read -- element; and --

Column 13,
Line 32, "sensor;" should read -- sensor; and --

UNITED STATES PATENT AND TRADEMARK OFFICE
CERTIFICATE OF CORRECTION

PATENT NO. : 6,304,784 B1
DATED : October 16, 2001
INVENTOR(S) : Allee et al.

It is certified that error appears in the above-identified patent and that said Letters Patent is hereby corrected as shown below:

<u>Column 14,</u>
Line 2, "actuator;" should read -- actuator; and --
Line 17, "device;" should read -- device; and --
Line 33, "valve;" should read -- valve; and --

Signed and Sealed this

Thirtieth Day of April, 2002

Attest:

Attesting Officer

JAMES E. ROGAN
*Director of the United States Patent and Trademark Office*